United States Patent
Ouchi et al.

(10) Patent No.: US 11,931,231 B2
(45) Date of Patent: *Mar. 19, 2024

(54) FOLDING DEVICE AND FOLDING METHOD

(71) Applicant: ZUIKO CORPORATION, Osaka (JP)

(72) Inventors: Masashi Ouchi, Osaka (JP); Yasutaka Tanaka, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 118 days.

This patent is subject to a terminal disclaimer.

(21) Appl. No.: 17/607,895

(22) PCT Filed: Apr. 24, 2020

(86) PCT No.: PCT/JP2020/017648
§ 371 (c)(1),
(2) Date: Oct. 31, 2021

(87) PCT Pub. No.: WO2020/226074
PCT Pub. Date: Nov. 12, 2020

(65) Prior Publication Data
US 2022/0273501 A1    Sep. 1, 2022

(30) Foreign Application Priority Data

May 7, 2019    (JP) .................. 2019-087491

(51) Int. Cl.
*A61F 13/15*    (2006.01)
*B65H 45/04*    (2006.01)

(52) U.S. Cl.
CPC ....... *A61F 13/15747* (2013.01); *B65H 45/04* (2013.01); *B65H 2701/1924* (2013.01)

(58) Field of Classification Search
CPC .............. A61F 13/15747; B65H 45/04; B65H 2701/1924; B65H 2801/57; B31F 1/0003; B31F 1/0006; B31F 1/0025; B31F 1/0029
(Continued)

(56) References Cited

U.S. PATENT DOCUMENTS

| 8,939,876 B2 * | 1/2015 | Schneider ......... A61F 13/15756 493/379 |
| 8,940,118 B2 * | 1/2015 | Schneider ......... A61F 13/15747 156/60 |

(Continued)

FOREIGN PATENT DOCUMENTS

| JP | 4354103 A | 8/2009 |
| JP | 6313101 A | 3/2018 |

(Continued)

OTHER PUBLICATIONS

International Search Report for corresponding Application No. PCT/JP2020/017648, dated Aug. 4, 2020.

*Primary Examiner* — Sameh Tawfik
(74) *Attorney, Agent, or Firm* — Renner, Otto, Boisselle & Sklar, LLP

(57) ABSTRACT

A plurality of folding units is arranged in a circumferential direction of a drum that rotates about an axis. Each of the folding units includes: a pad for holding one part of a workpiece on a pad surface; a first folding member and a second folding member each having a folding surface for folding a different part of the workpiece so as to stack the different part over the one part; and a pivot shaft arranged parallel to the pad surface. The first folding member, the second folding member, and the pivot shaft are configured to be rotated together until the folding surface reaches a facing position and a facing posture at which the folding surface faces the pad surface. The pivot shaft is configured to be displaced in a diameter direction of the drum crossing the pad surface.

10 Claims, 16 Drawing Sheets

(58) Field of Classification Search
USPC .......................................................... 493/405
See application file for complete search history.

(56) References Cited

U.S. PATENT DOCUMENTS

| | | | |
|---|---|---|---|
| 9,108,819 B2* | 8/2015 | Murakami | B65H 45/08 |
| 9,259,359 B2* | 2/2016 | Fujita | A61F 13/15747 |
| 11,039,961 B2* | 6/2021 | Long | A61F 13/496 |
| 2011/0287919 A1 | 11/2011 | Umebayashi | |
| 2011/0319243 A1 | 12/2011 | Fujita | |
| 2013/0029827 A1 | 1/2013 | Fujita | |
| 2021/0139252 A1* | 5/2021 | Viola | A61F 13/15764 |
| 2021/0267812 A1* | 9/2021 | Kreif | B65H 29/241 |
| 2022/0273501 A1* | 9/2022 | Ouchi | B65H 45/04 |
| 2022/0411204 A1* | 12/2022 | Piantoni | B65H 29/241 |

FOREIGN PATENT DOCUMENTS

| | | | | |
|---|---|---|---|---|
| JP | 2018070372 A | 5/2018 | | |
| WO | 2010089964 A1 | 8/2010 | | |
| WO | 2010119884 A1 | 10/2010 | | |
| WO | 2011152346 A1 | 12/2011 | | |
| WO | WO-2020226074 A1 * | 11/2020 | ....... | A61F 13/15747 |

\* cited by examiner

FIG. 4
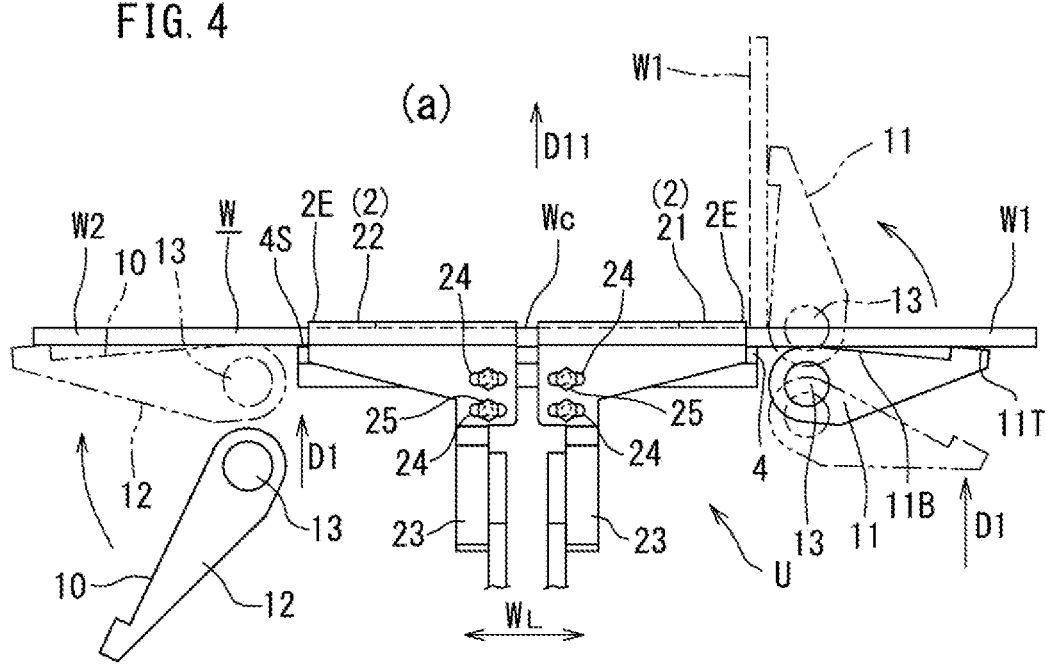
(a)
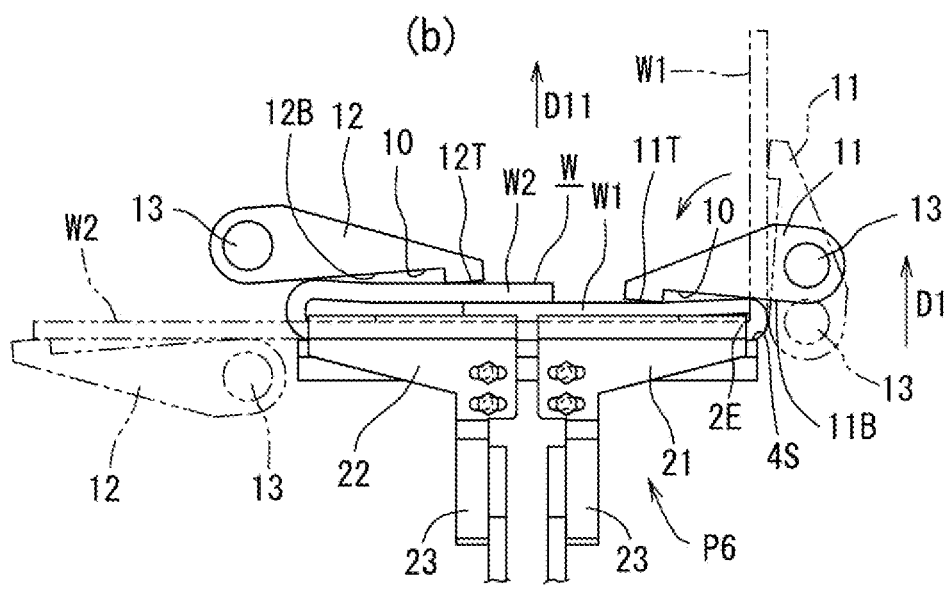
(b)

FIG.16
(a)
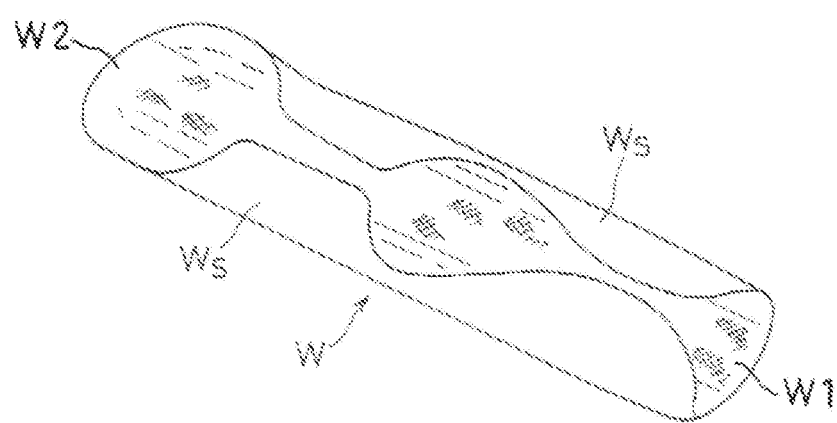
(b)
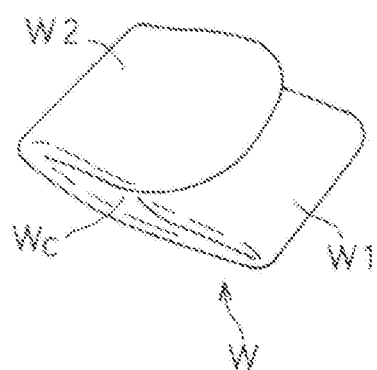

FOLDING DEVICE AND FOLDING METHOD

TECHNICAL FIELD

The present invention relates to a folding device and a folding method used for folding products, semifinished products, materials, etc., mainly of wearing items (sanitary napkins or incontinence pads, for example).

BACKGROUND ART

A folding mechanism or a folding device conventionally known includes a folding bar fixed to a tip of an arm to rotate about a predetermined rotation center, and the folding bar is used for folding a wearing item (first patent document and second patent document).

CITATION LIST

Patent Documents

First Patent document: JP 4,354,103 B
Second Patent document: JP 6,313,101 B

SUMMARY OF INVENTION

In the conventional folding device such as that of the arm type, however, trying to shorten time required for the folding by increasing the speed of the arm may cause a phenomenon that the folding bar gets caught on an item in returning from a folding position to an origin position at a speed exceeding a predetermined speed. This makes it impossible to fold the item into an intended shape due to the occurrence of creases in the item, for example, resulting in a risk that the item will become a defective.

Thus, the present invention is intended to provide a folding device and a folding method allowing folding of an item into a predetermined shape even at increased folding speed.

This folding device includes a plurality of folding units U arranged in a circumferential direction R of a drum 3 that rotates about an axis 31. Each of the folding units U includes:

a pad 4 for holding one part of a workpiece W on a pad surface 4S;

a first folding member 11 and a second folding member 12 each having a folding surface 10 for folding a different part of the workpiece W so as to stack the different part over the one part; and a pivot shaft 13 arranged parallel to the pad surface 4S, wherein the folding device is configured to:

rotate the first folding member 11 and the second folding member 12 with the pivot shaft 13 until the folding surface 10 reaches a facing position and a facing posture at which the folding surface 10 faces the pad surface 4S; and displace the pivot shaft 13 in a diameter direction D1 of the drum 3 crossing the pad surface 4S.

This folding method is a folding method of folding a workpiece W using a plurality of folding units U arranged in a circumferential direction R of a drum 3. The method includes:

a step of holding a center portion $W_C$ of the workpiece W on a pad surface 4S of the folding unit U;

a bending step of bending a first end portion W1 of the workpiece W by rotating a first folding member 11 for folding the first end portion W1 about a pivot shaft 13;

a pressing step of displacing the pivot shaft 13 in a diameter direction D1 of the drum 3 and pressing the workpiece W with the first folding member 11; and a first folding step of rotating a folding surface 10 of the first folding member 11 until the folding surface 10 comes to face the pad surface 4S via (across) the workpiece W so as to stack the first end portion W1 over the center portion $W_C$.

According to the above-described inventions, the function of holding the workpiece on the pad may be fulfilled through suction using negative pressure of air, the workpiece may be held using a large number of needles provided on a surface of the pad, for example, or the workpiece may be held with an extra hook.

According to the present invention, bending is started as the pivot shaft of the folding member is displaced in the diameter direction D1 of the drum. Thus, while the one part of the workpiece is held on the pad surface, the different part of the workpiece is pressed with the pivot shaft to define a folding line at a boundary between the one part and the different part and perform the bending step and the pressing step. Then, the workpiece is folded using the folding surface of the folding member so as to stack the one part over the different part.

In this way, the folding is performed after the folding line is defined. This eliminates a risk that the workpiece will get caught on the folding member when the folding member returns to an origin position. Thus, even at increased folding speed, the workpiece can still be folded into a predetermined while the occurrence of creases is reduced.

BRIEF DESCRIPTION OF DRAWINGS

FIG. 4 is a front view showing the motion of the folding unit at points P3 to P6;

FIG. 16 is a perspective view showing an example of a wearing item as a workpiece.

DESCRIPTION OF EMBODIMENTS

An embodiment of the present invention will be described below on the basis of the drawings. In the accompanying drawings, a number common to parts in a plurality of drawings means that these parts are equivalent or corresponding parts.

Figure 1:
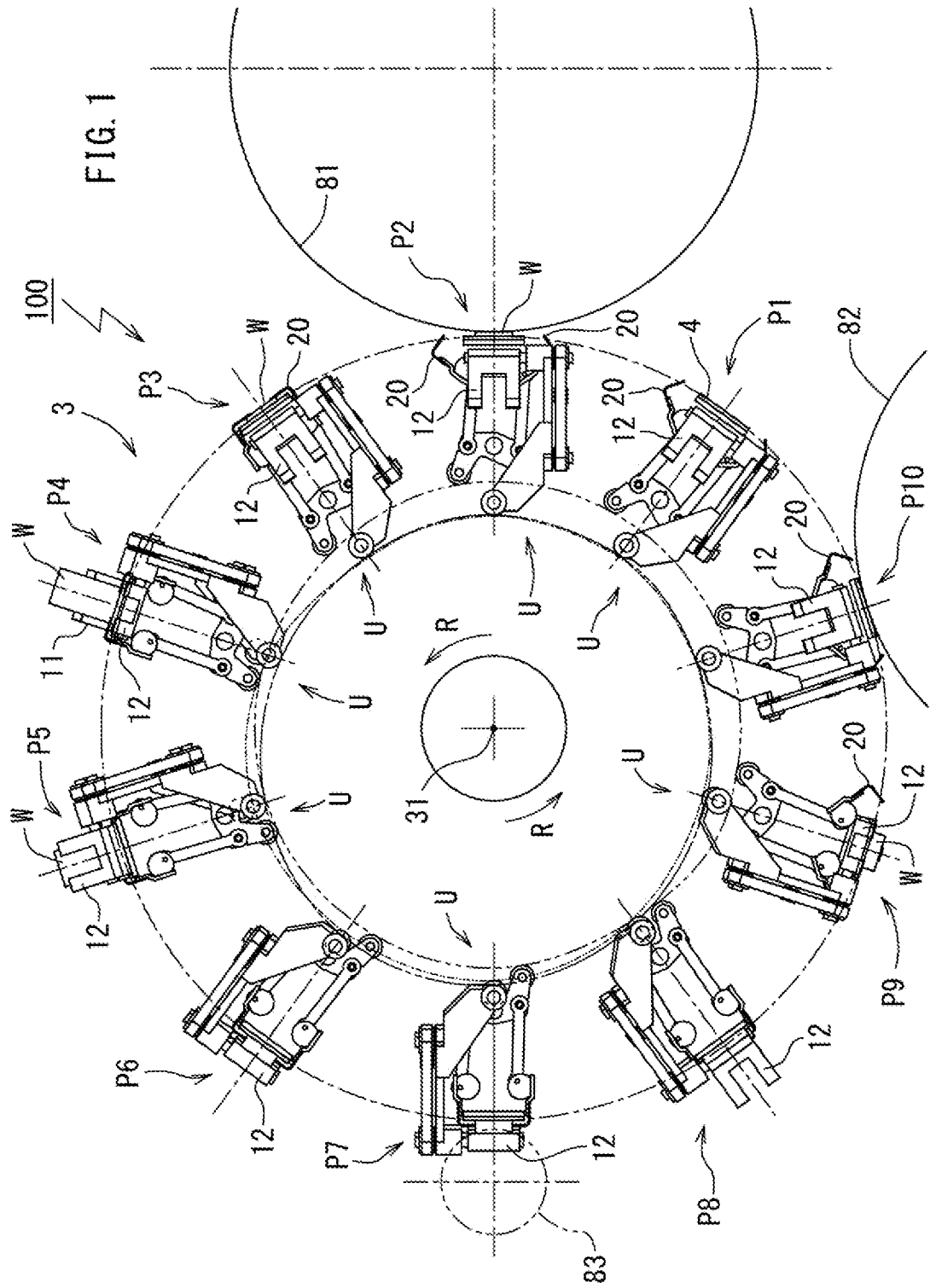
FIG. 1 is a schematic front view of a folding device showing one embodiment of the present invention.

As shown in FIG. 1, a folding device 100 according to one embodiment of the present invention includes a drum 3 that rotates an axis 31, and a plurality of folding units U. All the folding units U are arranged on the drum 3 in a circumferential direction R.

During one rotation from an origin (point P1) (until return to the same point P1), each folding unit U receives a workpiece W from a first transport device 81 at a point P2, folds the workpiece W at points P3 to P7, ad transfers the folded workpiece W to a second transport device 82 at a point P10.

The states of the folding unit U at the points P1 to P10 in FIG. 1 are shown in FIGS. 5 to 14 respectively.

The workpiece W will be descried next. As shown in FIG. 16(a), the workpiece W is an elongated item such as a sanitary napkin, for example. The workpiece W has both sides $W_S$ extending in a lengthwise direction and the both sides $W_S$ are folded toward a center of a width direction. In the present embodiment, the workpiece W is folded so as to stack each of a first end portion W1 and a second end portion W2 over a center portion $W_C$.

In FIGS. 1 to 15, for the convenience of drawing, the workpiece W is illustrated as a part having a flat plate shape.

Figure 3:
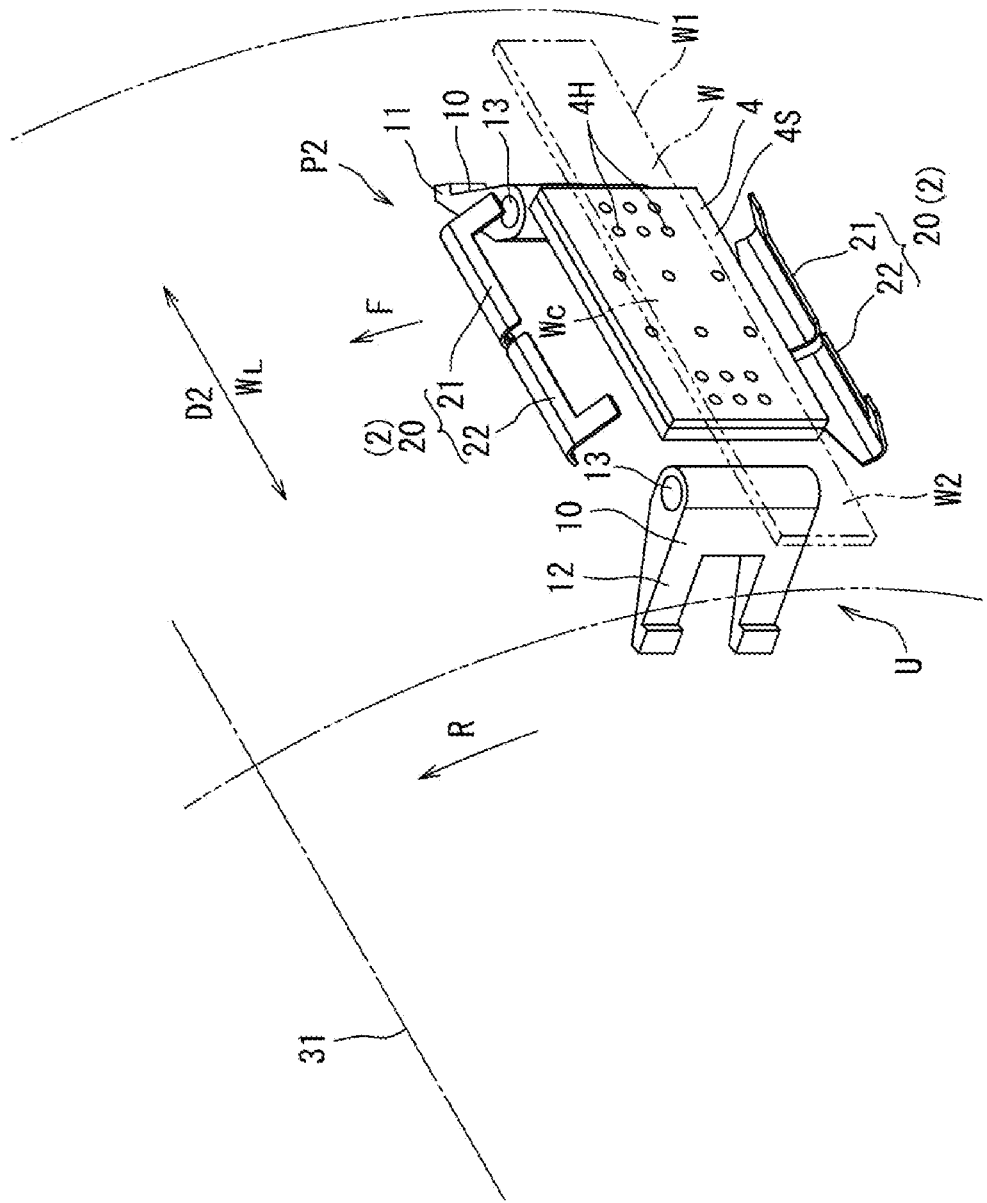
FIG. 3 is a perspective view showing the folding unit at a point P2 together with a part of a drum.

The following describes the location of the drum 3 and those of principal parts of the folding unit U relative to each other by referring to FIG. 3.

As shown in FIG. 3, each folding unit U includes a pad 4, a first folding member 11, a second folding member 12, and a retaining mechanism 2.

The pad 4 is attached in a removable manner to the folding unit U and is replaced, if appropriate, in response to the size (length in a lengthwise direction $W_L$) of the workpiece W.

The pad 4 has a pad surface 4S provided with a large number of suction holes 4H. In the present embodiment, the center portion $W_C$ of the workpiece W is sucked on the pad surface 4S through the suction holes 4H connected to a vacuum not shown in the drawings to be held on the pad 4. In the present embodiment, end portions of the workpiece W on the both sides, namely, the first end portion W1 and the second end portion W2 protrude from the pad 4 in a state of not being held on the pad 4.

The first folding member 11 and the second folding member 12 in FIG. 3 are arranged adjacent to the short sides of the rectangular pad 4. More specifically, the first folding member 11 and the second folding member 12 in their non-folding states are arranged adjacent to the first end portion W1 and the second end portion W2 respectively of the workpiece W as viewed in the lengthwise direction $W_L$. The first folding member 11 and the second folding member 12 each pivot about a pivot shaft 13. The first folding member 11 and the second folding member 12 each have a folding surface 10 for folding the workpiece W.

Figure 13:
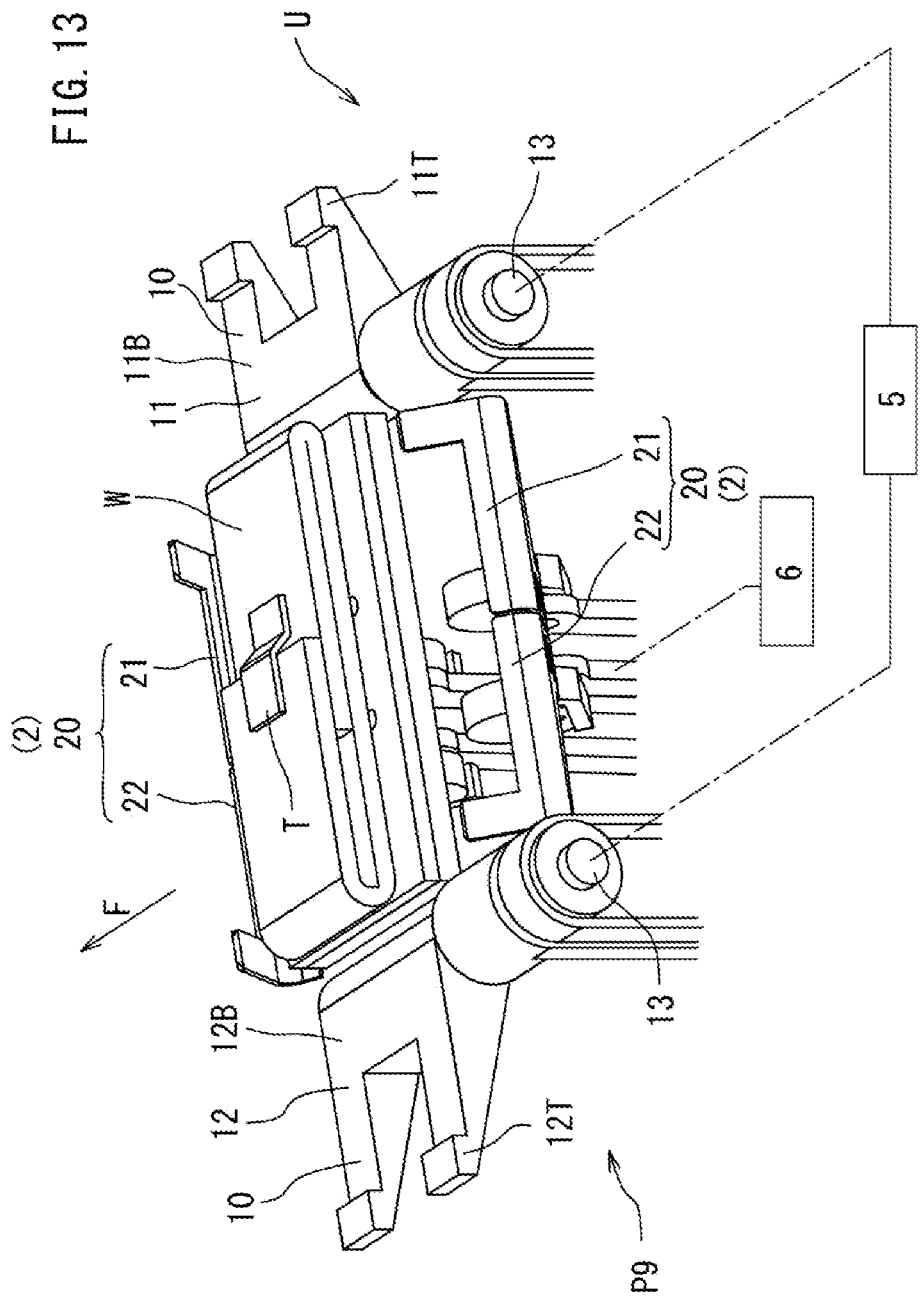
FIG. 13 is a perspective view of the folding unit at a point P9.

As explicitly shown in FIG. 13, the first folding member 11 is formed into a U shape in a top view, and has a tip 11T away from the pivot shaft 13 and a base 11B close to the pivot shaft 13. The tip 11T projects toward a direction of a normal to the folding surface 10 in comparison with the folding surface 10 on the side of the base 11B.

The second folding member 12 is formed into a U shape in a top view, and has a tip 12T away from the pivot shaft 13 and a base 12B close to the pivot shaft 13. The tip 12T projects toward a direction of a normal to the folding surface 10 in comparison with the folding surface 10 on the side of the base 12B.

The shapes of the first folding member 11 and the second folding member 12 in a top view are not limited to the U shapes but may be rectangular shapes or other shapes.

At least one of the first folding member 11 and the second folding member 12 in FIG. 3 is made movable in a width direction D2 parallel to the axis 31 of the drum 3 by a position adjusting mechanism not shown in the drawings and is adjusted in position, if appropriate, in response to the size of the workpiece W (length in the lengthwise direction $W_L$).

As shown in FIG. 4, the first folding member 11 and the second folding member 12 fold the first end portion W1 and the second end portion W2 of the workpiece W respectively so as to stack the first end portion W1 and the second end portion W2 over the center portion $W_C$ (see FIGS. 7 to 10).

In FIG. 3, the pad 4, the first folding member 11, and the second folding member 12 are arranged at the same position as viewed in the circumferential direction R.

The width direction D2 of the drum 3 parallel to the axis 31 is defined in the lengthwise direction $W_L$ of the workpiece W. This allows reduction in a pitch between the pads 4 belonging to the plurality of folding units U and next to each other in the circumferential direction R, as shown in FIG. 1. By doing so, it becomes possible to arrange a large number of pads 4 on the drum 3 in the circumferential direction R, thereby encouraging increase in the number of items produced per unit time.

The retaining mechanism 2 in FIG. 2 will be described next in detail.

Figure 2:
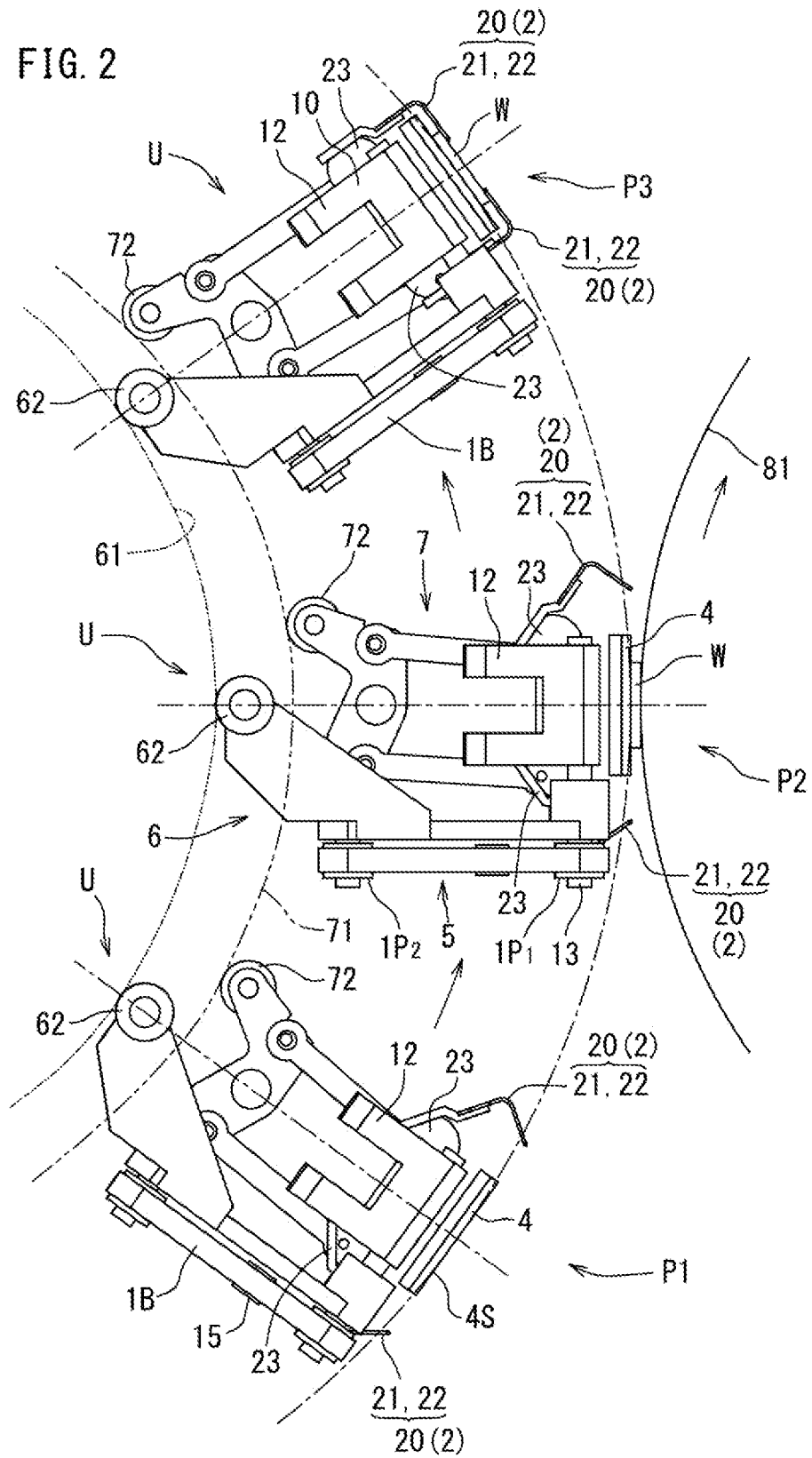
FIG. 2 is a front view of each folding unit at points P1 to P3.

As shown in FIGS. 2 to 5, the retaining mechanism 2 in FIG. 2 includes retaining parts 20 in a pair, a pivot frame 23, and a pivot mechanism not shown in the drawings.

One of the retaining parts 20 is arranged on a front side F of a rotation direction conforming to the circumferential direction R, and the other retaining part 20 is arranged on a back side B of the rotation direction conforming to the circumferential direction R. More specifically, the retaining parts 20 are arranged adjacent to respective long sides of the pad 4 in FIG. 3.

As shown in FIGS. 3 to 15, each retaining part 20 includes a first retaining plate 21 and a second retaining plate 22 resulting from division of the retaining part 20 into two in the lengthwise direction $W_L$.

Figure 15:
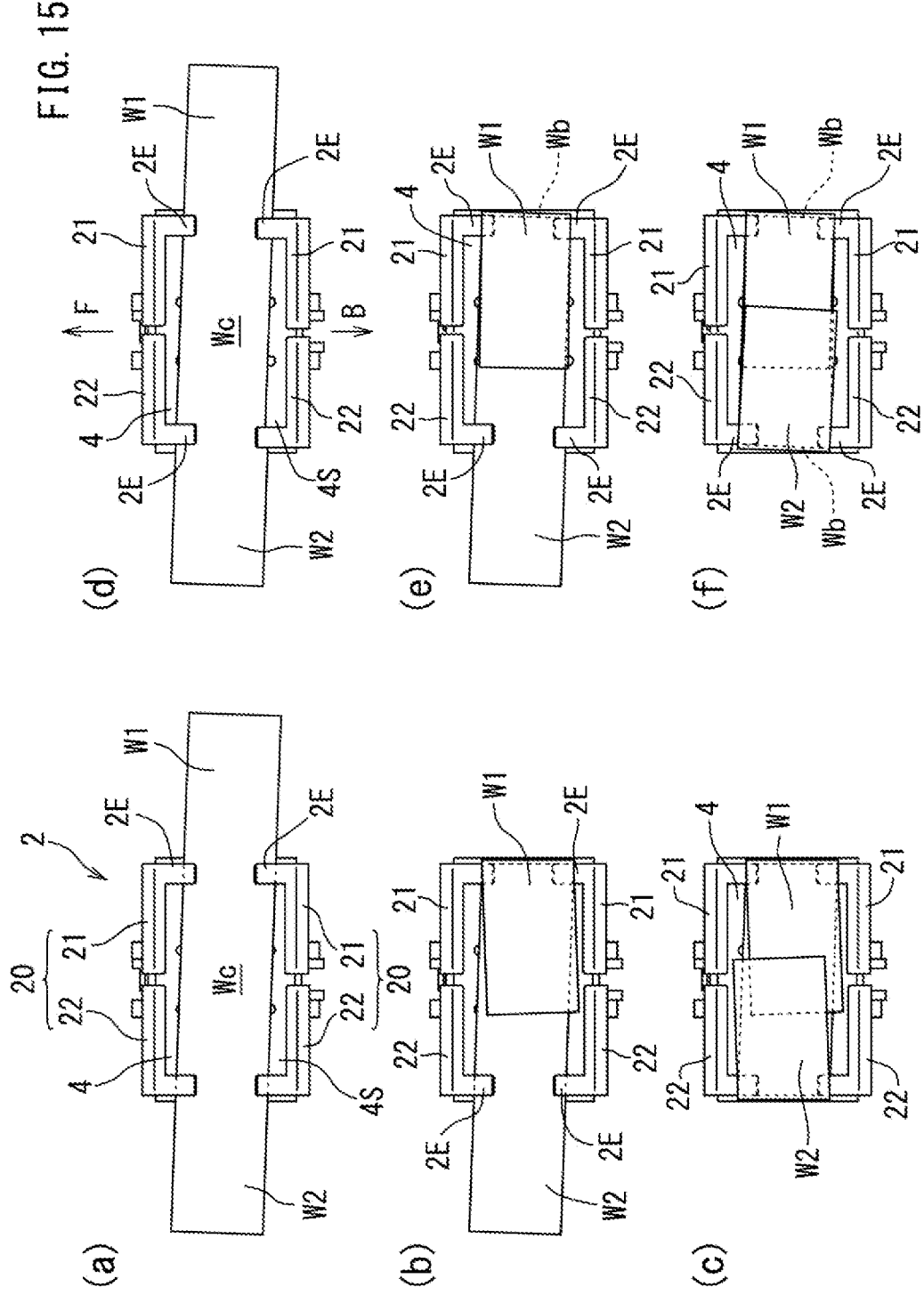
FIG. 15 is a plan view showing a folding method.

As shown in FIG. 15, the first retaining plate 21 and the second retaining plate 22 are formed into L shapes (L shape and reversed L shape) in a top view. Thus, when the retaining parts 20 in a pair come to face or contact an exposed surface of the workpiece W, the first retaining plate 21 and the second retaining plate 22 of one of the retaining parts 20 and the first retaining plate 21 and the second retaining plate 22 of the other retaining part 20 form a rectangular frame to define a pair of folding lines Wb in the workpiece W (FIG. 15(f)).

In FIG. 4, the first retaining plate 21 and the second retaining plate 22 each have a long hole 24 and is fixed to the pivot frame 23 with a fixing bolt 25 passing through the long hole 24.

The long hole 24 in FIG. 4 is formed to extend in the lengthwise direction $W_L$. Thus, loosening the fixing bolt 25, moving at least one of the first retaining plate 21 and the second retaining plate 22 in the lengthwise direction $W_L$, and then fastening the fixing bolt 25 again allows adjustment of the position of the retaining part 20 in the lengthwise direction $W_L$.

By doing so, it becomes possible to adjust the positions of the end portion 2E of the first retaining plate 21 and/or the end portion 2E of the second retaining plate 22 as viewed in the lengthwise direction $W_L$. This makes the position of each folding line Wb in the lengthwise direction $W_L$ freely settable in response to the size of the workpiece W (length in the lengthwise direction $W_L$).

The following describes how the first folding member 11 and the second folding member 12 are driven.

Each folding unit U includes a first driving part 5 (omitted from the drawings) provided for each of the first folding member 11 and the second folding member 12.

As shown in FIGS. 7 to 10, the first driving part 5 causes the first folding member 11, the second folding member 12, and the pivot shaft 13 to pivot together until the folding surface 10 reaches a facing position and a facing posture at which the folding surface 10 faces the pad surface 4S.

As shown in FIG. 4, the first driving part displaces the pivot shaft 13 in a diameter direction D1 of the drum 3 (a direction crossing the pad surface 4S). The pivot shaft 13 in FIG. 5 is arranged parallel to the pad surface 4S.

In the above-described configuration, in response to the motion of the first driving part 5, the pivot shaft 13 in FIG. 4 moves to be on an outer side D11 of the diameter direction D1 outside more than (in comparison with) the pad surface 4S. Then, the first folding member 11 and the second folding member 12 rotate to the facing position at which the folding surfaces 10 face the pad surface 4S.

The following describes how the retaining part 20 is driven.

Figure 5:
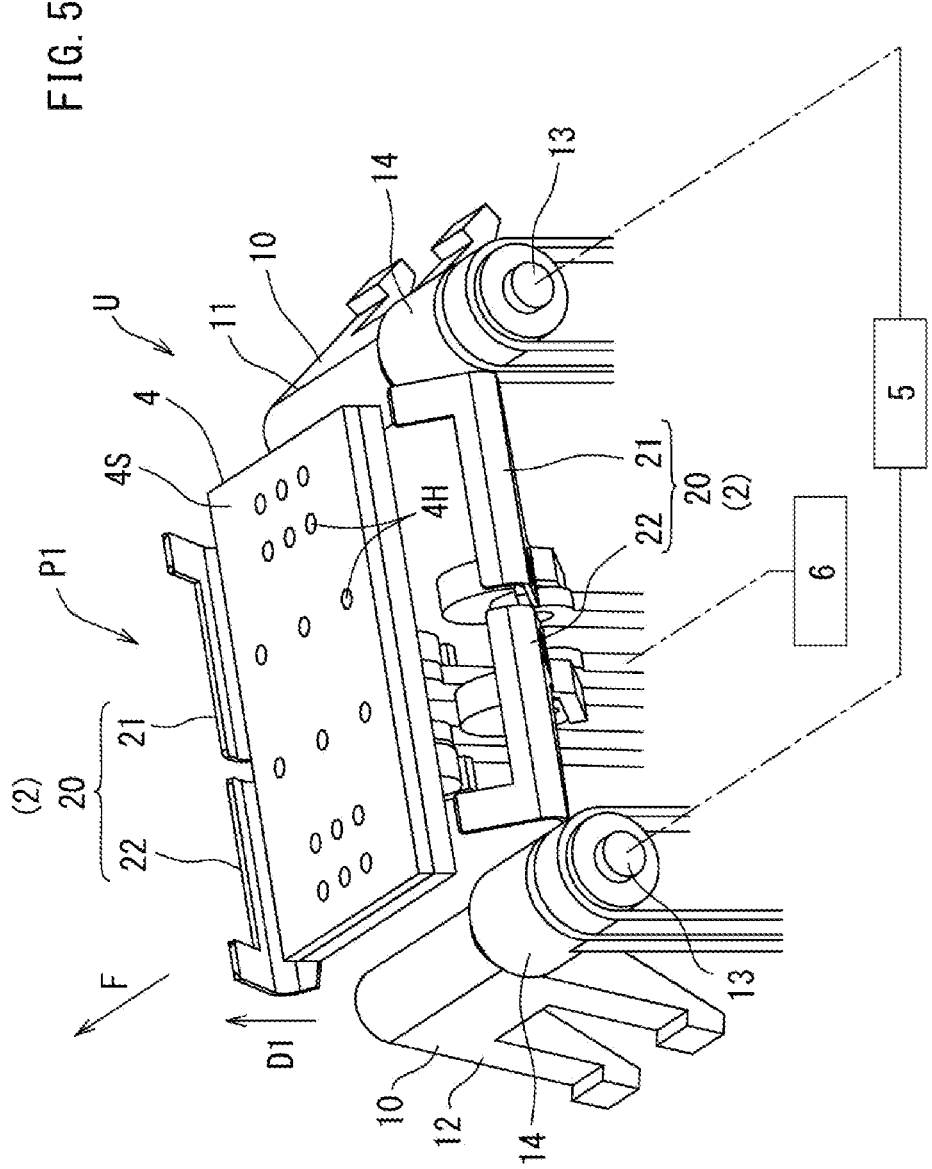
FIG. 5 is a perspective view of the folding unit at a point P1 showing the embodiment.
Figure 6:
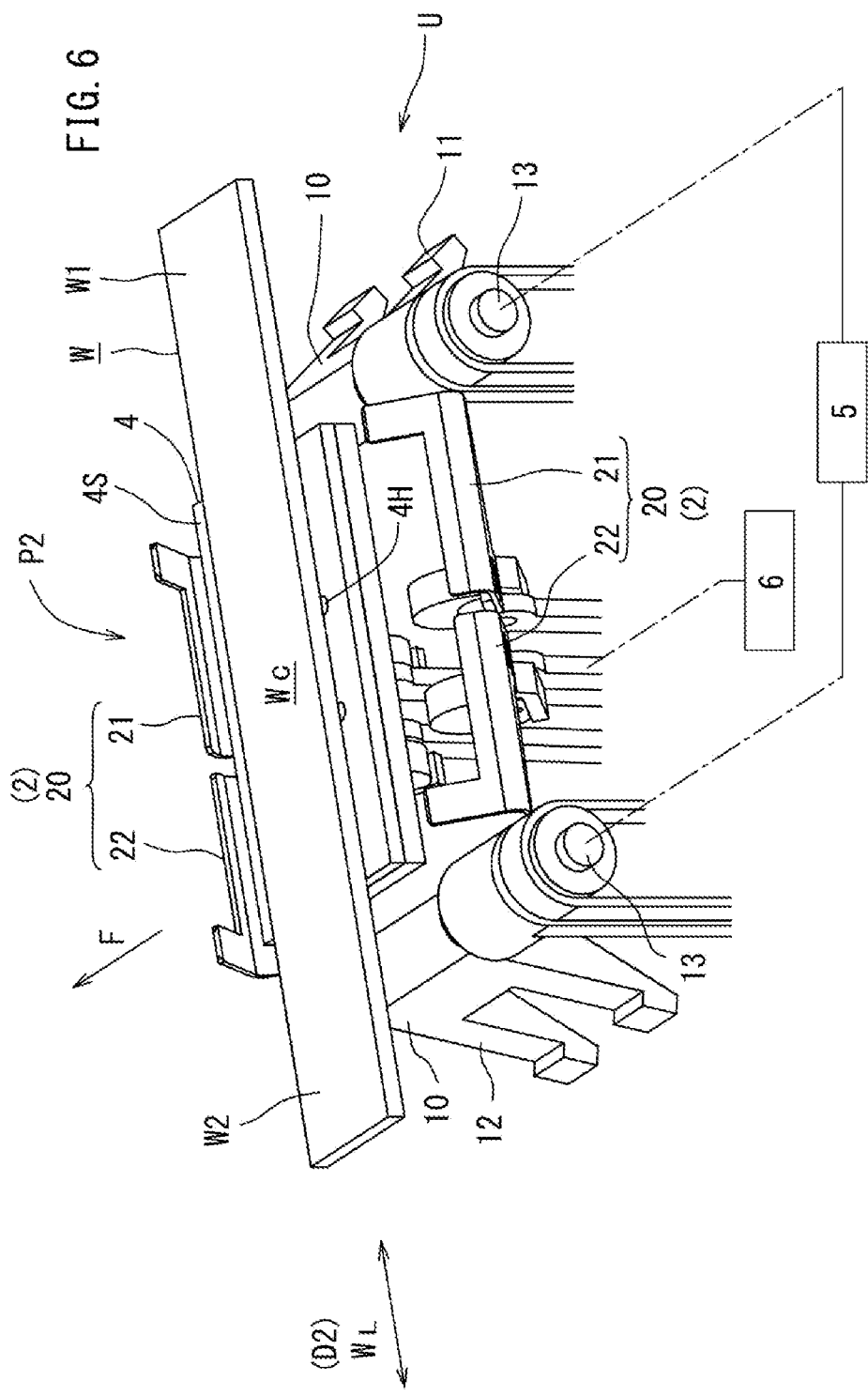
FIG. 6 is a perspective view of the folding unit at the point P2.

As shown in FIG. 5, each folding unit U includes a second driving part 6. The second driving part 6 rotates the retaining part 20 in such a manner that the retaining part 20 in FIG. 5 rotates from a position spaced apart (separated) from the pad 4 as viewed in the circumferential direction R (FIG. 3) to face or contact the exposed surface of the workpiece W in FIG. 7.

As a result of the above-described motion, while the center portion $W_C$ of the workpiece W in FIG. 4 is held on the pad 4, the first folding member 11 and the second folding member 12 sequentially bend the first end portion W1 and the second end portion W2 of the workpiece W while contacting the first end portion W1 and the second end portion W2 respectively. By doing so, the first end portion W1 is folded so as to be stacked over the center portion $W_C$, and then the second end portion W2 is further folded so as to be stacked over the first end portion W1 and the center portion $W_C$.

The folding of the workpiece W by the folding device 100 will be described next.

At the point P1 (FIG. 1, etc.) that is an origin position in FIG. 2, the retaining mechanism 2, the first folding member 11, and the second folding member 12 are in fully-opened states (FIG. 5, etc.). At the point P1, suction of air through the suction holes 4H at the pad 4 is started. Furthermore, the drum 3 rotates about the axis 31 to move the folding unit U at the point P1 toward the point P2.

At the point P2 in FIG. 2 that is a receiving position of receiving the workpiece W before being folded, the folding unit U receives the workpiece W onto the pad 4 (FIG. 1, etc.). The workpiece W in FIG. 3 moves from the first transport device 81 (FIG. 1) to the folding unit U while the workpiece W faces the pad 4 in a posture at which the width direction D2 of the drum 3 and the lengthwise direction $W_L$ of the workpiece W become substantially parallel to each other, and the center portion $W_C$ of the workpiece W is sucked on the pad 4.

In the present embodiment, as shown in FIG. 2, the receiving position (point P2) is set at a position just beside the drum 3 (a position on a horizontal extension line passing through the axis 31), for example.

The retaining mechanism 2, the first folding member 11, and the second folding member 12 are also in the fully-opened states at the point P2 in FIG. 3. The folding unit U at the point P2 continues moving from the point P2 toward a point P3 in FIG. 2.

During the move of the folding unit U from the point P2 to the point P3 in FIG. 2, the retaining parts 20 in a pair rotate to directions opposite each other to be closed.

More specifically, the retaining part 20 on the front side rotates in a reverse direction of the circumferential (rotation) direction R, and the retaining part 20 on the back side rotates in a positive direction of the circumferential (rotation) direction R.

Figure 7:
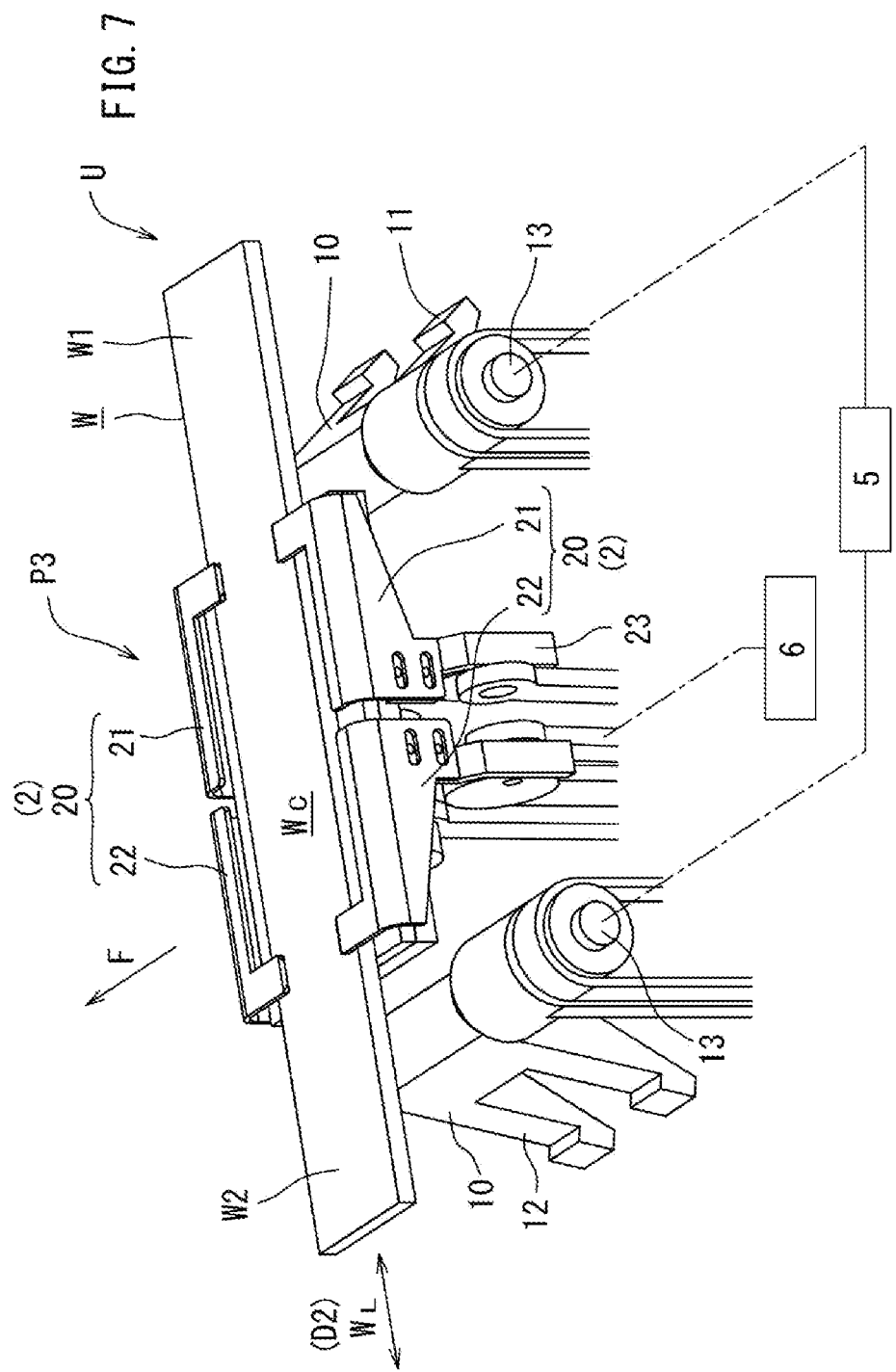
FIG. 7 is a perspective view of the folding unit at a point P3.
Figure 8:
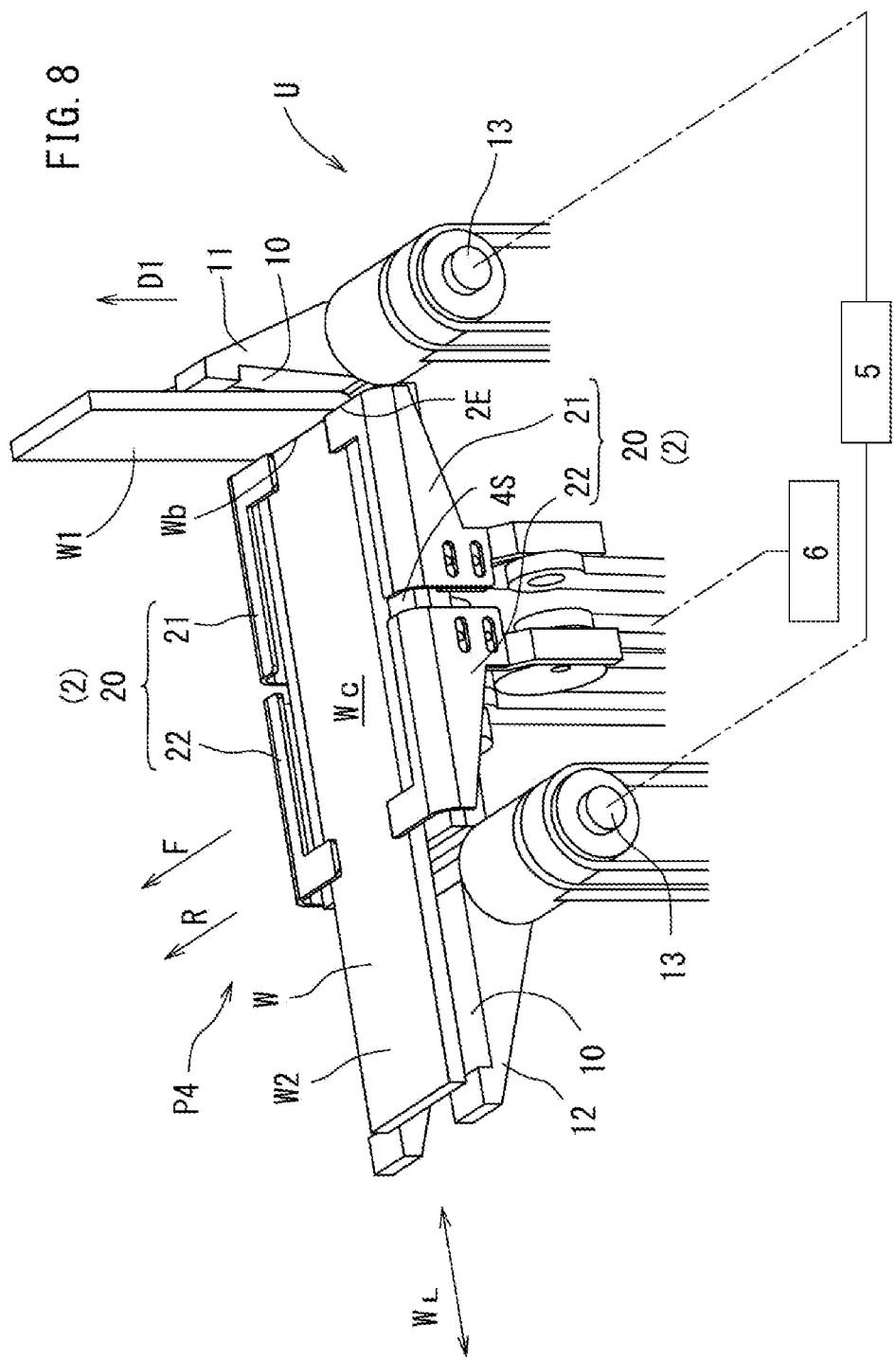
FIG. 8 is a perspective view of the folding unit at a point P4.

By doing so, when the first retaining plates 21 and the second retaining plates 22 of both the retaining parts 20 in FIG. 7 come to face or contact the center portion $W_C$ (exposed surface) of the workpiece W, the first retaining plates 21 and the second retaining plates 22 are formed into a rectangular frame-like shape to define the folding lines Wb of the workpiece W (FIG. 8).

The first retaining plate 21 and the second retaining plate 22 preferably contact the workpiece W to such a degree as to press the surface of the workpiece W loosely.

The first folding member 11, and the second folding member 12 are also in the fully-opened states at the point P3 in FIG. 3. The folding unit U at the point P3 continues moving from the point P3 toward a point P4 (FIG. 1).

During the move of the folding unit U from the point P3 to the point P4 in FIG. 1, the pivot shaft 13 of the first folding member 11 in FIG. 4 is displaced in the diameter direction D1 of the drum 3 to perform a pressing step of pressing the folding surface 10 of the first folding member 11 against the first end portion W1 of the workpiece W and a bending step of bending the first end portion W1 of the workpiece W by causing the first folding member 11 to pivot about the pivot shaft 13.

On the other hand, during the move of the folding unit U from the point P3 to the point P4 in FIG. 1, the pivot shaft 13 of the second folding member 12 is displaced in the diameter direction D1 and the second folding member 12 rotates to a position at which the folding surface 10 of the second folding member 12 is arranged on the substantially same plane as the pad surface 4S, as shown in FIG. 4(a). Specifically, the second end portion W2 of the workpiece W is in a state yet to be folded.

The bending by the first folding member 11 will be described in detail using FIG. 4.

As shown in FIG. 4(a), during rotation of the first folding member 11 toward a closing direction, the base 11B close to the pivot shaft 13 moves toward the outer side of the diameter direction D1 to simultaneously perform the pressing step and the bending step as shown in FIG. 4(a), the pressing step pressing the folding surface 10 of the first folding member 11 against the first end portion W1 of the workpiece W, and the bending step bending the first end portion W1 of the workpiece W by causing the first folding member 11 to pivot about the pivot shaft 13.

During implementations of these two steps, the first folding member 11 is bent (rotated) using the end portion (one end portion) 2E of the retaining mechanism 2 in FIG. 8 as viewed in the lengthwise direction $W_L$ as a reference for a folding line (one folding line) of the workpiece W. This motion is also applied to the second folding member 12.

While the workpiece W in FIG. 4(a) is sucked on the pad 4 at the center portion $W_C$ and is pressed from above by the retaining mechanism 2, the first end portion W1 is pressed in the diameter direction D1 by the base 11B of the first folding member 11 in the vicinity of the end portion 2E of the first retaining plate 21.

By doing so, as shown in FIG. 4, the folding line Wb (FIG. 8) is defined between the center portion $W_C$ and the first end portion W1. By folding the first end portion W1 of the workpiece W with the folding line defined in this way using the first folding member 11, creases are unlikely to be caused in the workpiece even during bending of the workpiece W at high speed.

Next, the folding unit U in FIG. 1 moves from the point P4 toward a point P5. At this time, the first folding member 11 in FIG. 9 folds the first end portion W1 and the second folding member 12 bends the second end portion W2.

Figure 9:
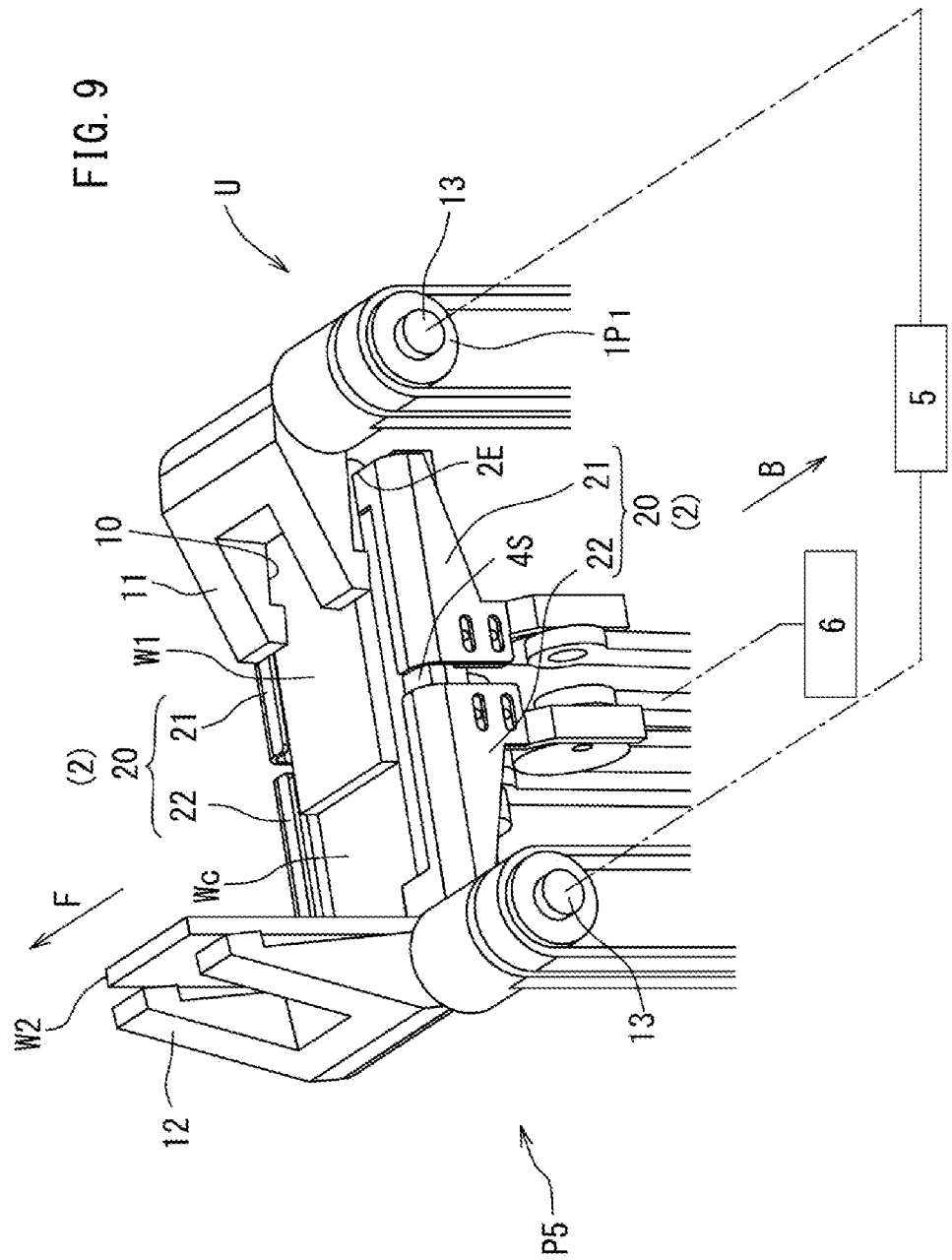
FIG. 9 is a perspective view of the folding unit at a point P5.
Figure 10:
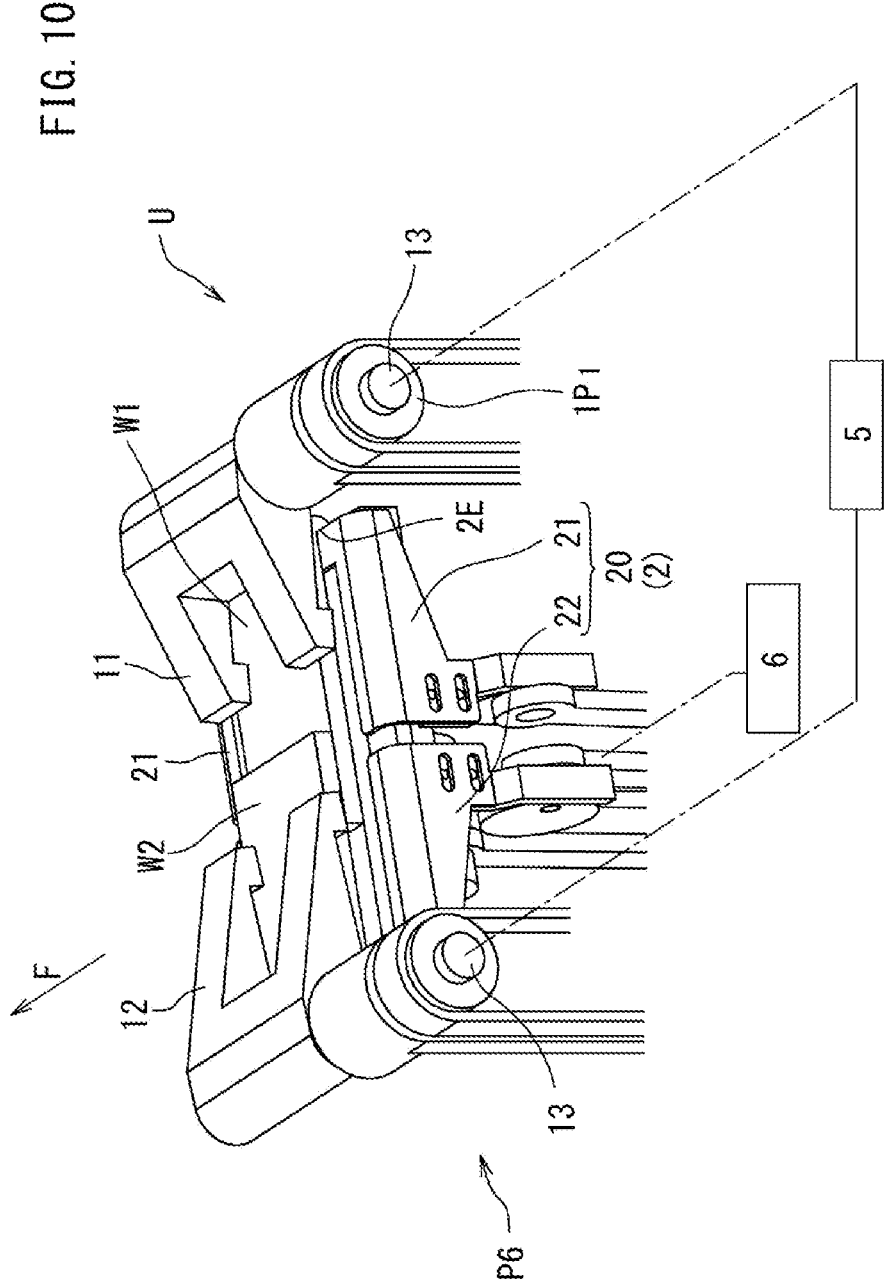
FIG. 10 is a perspective view of the folding unit at a point P6.

Then, a first folding step is performed in which the folding surface 10 of the first folding member 11 in FIG. 10 rotates until it comes to face the pad surface 4S across (via) the workpiece W so as to stack the first end portion W1 in FIG. 9 over the center portion $W_C$.

In the pressing step, the bending step by the first folding member 11, and the first folding step described above, the workpiece is bent continuously while the folding surface 10 of the first folding member 11 in FIGS. 4(a) and (b) is in surface contact with the first end portion W1 of the workpiece W.

Each of these steps is performed while the center portion $W_C$ of the workpiece W is sucked on the pad surface 4S and the first end portion W1 of the workpiece W is in a non-sucked state of not being sucked on the folding surface 10 of the first folding member 11.

As shown in FIG. 9, a second bending step is performed in which the second end portion W2 of the workpiece W is bent by the second folding member 12. The second bending step will not be described as it is performed in the same way as the above-described bending step by the first folding member 11.

The folding by the first folding member 11 will be described.

As shown in FIG. 4(b), during folding of the workpiece W, the first folding member 11 rotates about the pivot shaft 13 and the pivot shaft 13 moves toward the outer side of the diameter direction D1. Thus, the workpiece W is bent like a hairpin in the vicinity of the end portion 2E of the first retaining plate 21. As a result, even if the workpiece W has a great thickness, folding of the workpiece W is facilitated.

Next, the folding unit U in FIG. 1 moves from the point P5 toward a point P6. At this time, the second folding member 12 folds the second end portion W2 while the folded state of the first end portion W1 is maintained by the first folding member 11 in FIG. 10.

In this way, a second folding step is performed in which the second end portion W2 of the workpiece W is folded so as to be stacked over the folded first end portion W1. A second pressing step, a bending step, and a folding step by the second folding member 12 will not be described as they are performed in the same way as the corresponding steps performed by the first folding member 11.

As shown in FIG. 4(b), while the respective folding surfaces 10 of the first folding member 11 and the second folding member 12 are in postures of facing the pad surface 4S, the pivot shaft 13 of the second folding member 12 may be located on the outer side D11 outside more than the pivot shaft 13 of the first folding member 11.

Figure 11:
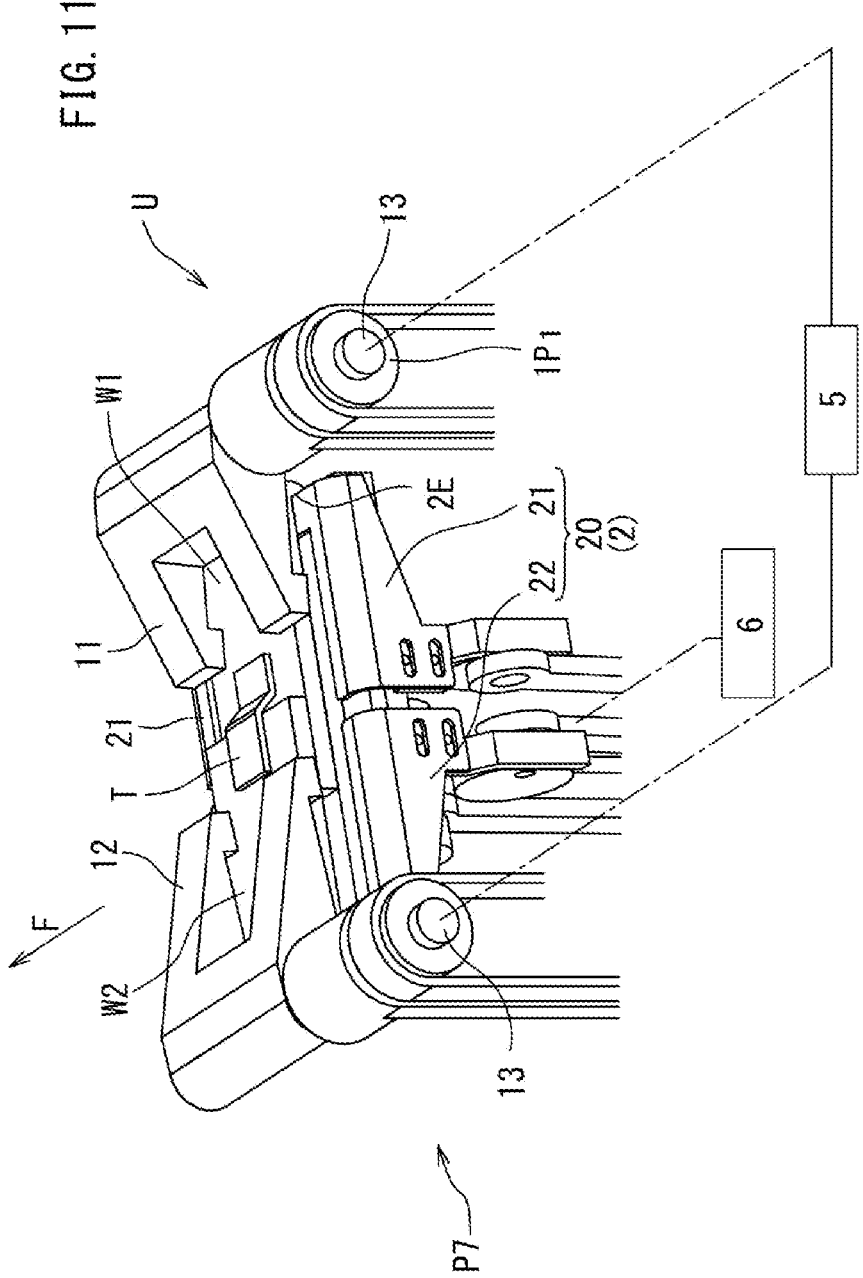
FIG. 11 is a perspective view of the folding unit at a point P7.

Next, the folding unit U in FIG. 1 moves from the point P6 toward a point P7. At this time, as shown in FIG. 11, while the first folding member 11 and the second folding member 12 press the first end portion W1 and the second end portion W2 of the workpiece W respectively, tape T is affixed by an affixing device 83 (FIG. 1) in such a manner as to extend over the first end portion W1 and the second end portion W2.

Figure 12:
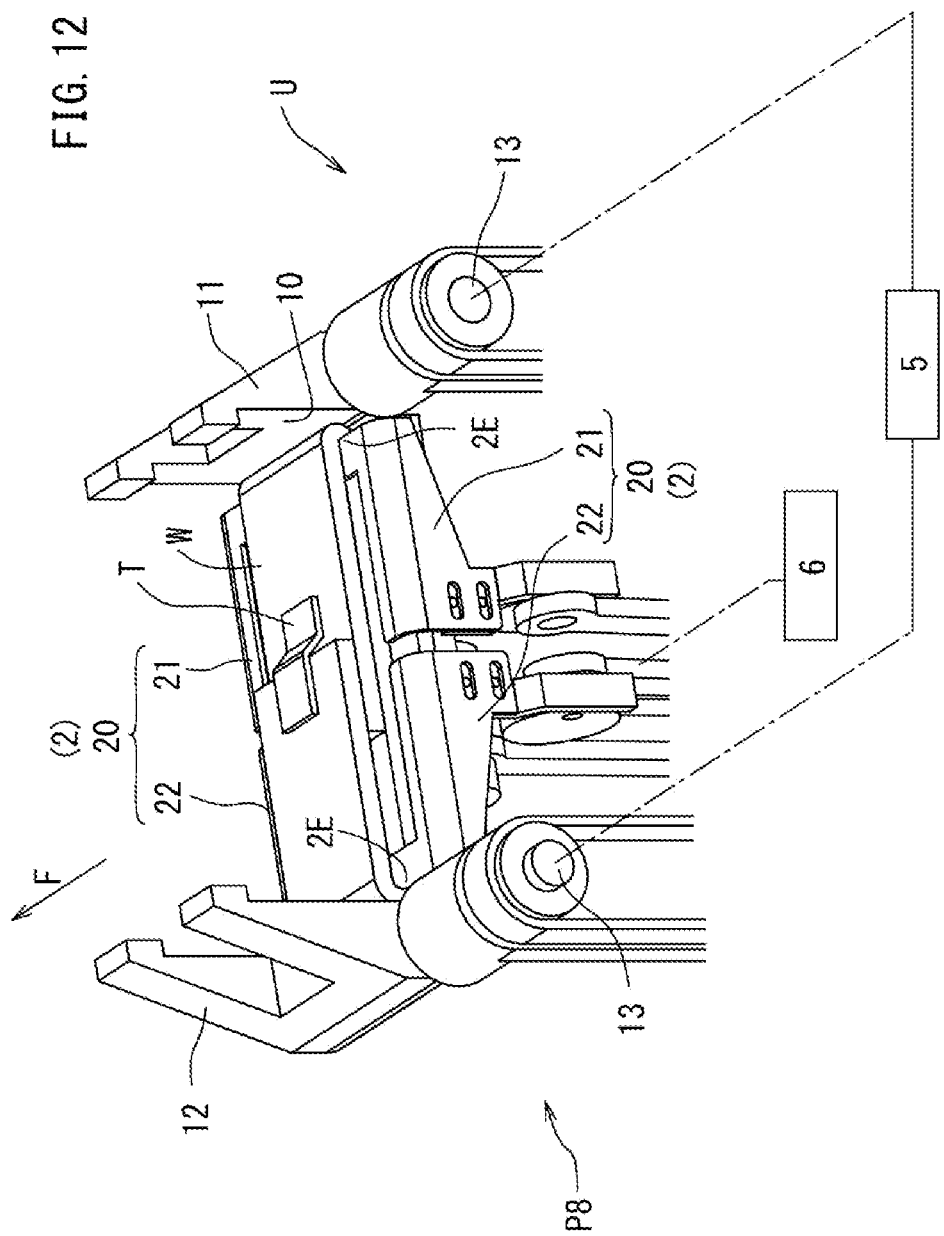
FIG. 12 is a perspective view of the folding unit at a point P8.

Next, the folding unit U in FIG. 1 moves from the point P7 to a point P9 after passing through a point P8. At this time, the pair of folding members (first folding member 11, second folding member 12) in FIGS. 12 and 13 are opened to be separated from the workpiece W, and the retaining mechanism 2 is opened to be separated from the workpiece W.

Figure 14:
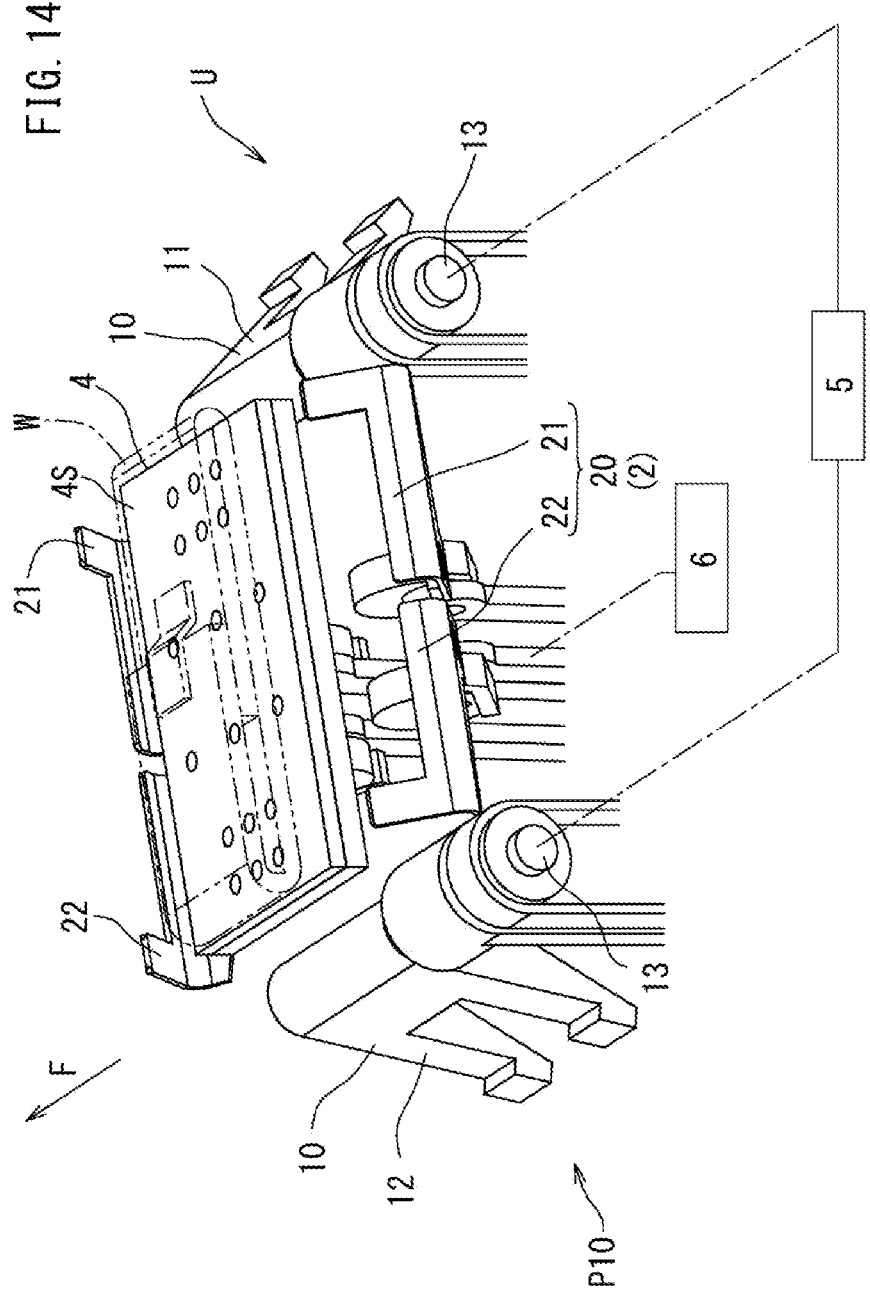
FIG. 14 is a perspective view of the folding unit at a point P10.

Next, the folding unit U in FIG. 1 moves from the point P9 toward the point P10 and finishes holding of the workpiece W under suction in FIG. 14 at the point P10 (a vacuum not shown in the drawings is stopped). At the same time, the workpiece W is transferred from the folding unit U to the second transport device 82 in FIG. 1 at the point P10.

Then, the folding unit U in FIG. 1 moves from the point P10 to reach the point P1 again as an origin position, and receives a next workpiece W from the first transport device 81.

In the above-described embodiment, the step of defining the folding line of the workpiece W using the retaining mechanism 2 is finished before the first folding member 11 and the second folding member 12 in FIG. 7 start folding of the workpiece W. However, this is not the only case. The step of defining the folding line of the workpiece W using the retaining mechanism 2 has only to be finished before the first folding member 11 or the second folding member 12 finishes folding of the workpiece W.

Any one of the steps of opening the first folding member 11, the second folding member 12, and the retaining part 20 at the point P8 and the point P9 in FIG. 1 may be performed previously, or these steps may be performed simultaneously.

In the present embodiment, the folded workpiece W is transferred from the folding unit U to the second transport device 82 at the point P10. However, this is not the only case. The folded workpiece W may be transferred from the folding unit U to the second transport device 82 at any point, as long as the pair of folding members (first folding member 11, second folding member 12) have been opened to be separated from the workpiece W and the retaining mechanism 2 has been opened to be separated from the workpiece W at this point (point P8 or point P9).

The following describes a case where the position of a folding line is changed using the end portion 2E of the retaining part 20 in FIG. 8.

The position of the folding line is changed in response to change in the type of the workpiece W and is also changed in the following case.

In this example, as shown in FIGS. 1 and 3, the workpiece W is received in a horizontally-long state while only the center portion $W_C$ of the workpiece is sucked on the pad 4. Hence, if the first end portion W1 or the second end portion W2 of the workpiece is heavy, for example, the workpiece W may be sucked on the pad 4 while being tilted from the pad surface 4S, as shown in FIG. 15(a).

Folding the workpiece W in this state as shown in FIGS. 15(a) to (c) results in a bad folded state of the workpiece as shown in FIG. 15(c), and this may cause reduction in a product value or the workpiece may easily be bulky during packing.

In this regard, the following technique may be employed for improving a folded state of a workpiece.

As described above, the first retaining plate 21 and the second retaining plate 22 of the retaining part 20 in FIG. 4(a) are defined as a result of division of the retaining part 20 into two in the lengthwise direction $W_L$ and are fixed with the bolt 25 to the pivot frame 23 so as to be changeable in position in the lengthwise direction $W_L$. This allows the positions of the respective end portions 2E of the first retaining plate 21 and the second retaining plate 22 as viewed in the lengthwise direction $W_L$ to be changed in response to a workpiece.

As shown in FIG. 15(d), if the workpiece W is tilted from the pad 4, for example, the second retaining plate 22 on the front side F and the first retaining plate 21 on the back side B at diagonal corners are fixed at positions closer to the center of the workpiece W.

Specifically, the second retaining plate 22 on the front side F is fixed at a position closer to the center than the second retaining plate 22 on the back side B, and the first retaining plate 21 on the back side B is fixed at a position closer to the center than the first retaining plate 21 on the front side F. By doing so, the folding line Wb of the first end portion W1 in FIG. 15(e) and the folding line Wb of the second end portion W2 in FIG. 15(f) become parallel to each other and become diagonal to the pad 4. In this way, a folded state of the workpiece is improved.

Technical ideas and advantageous effects understandable from the above-described embodiment will be described next.

In a preferred device, the first driving part 5 rotates the first folding member 11 and the second folding member 12 until the folding surface 10 reaches a facing position at which the folding surface 10 faces the pad surface 4S after the first driving part 5 moves the pivot shaft 13 to cause the pivot shaft 13 to be positioned on the outer side D11 of the diameter direction D1 outside more than the pad surface 4S.

In this case, a different part of the workpiece W is folded on one part of the workpiece W after being displaced toward the outer side of the diameter direction. Thus, even if the workpiece W is a thick item such as a wearing item, creases will still be unlikely to occur after the folding.

More preferably, the first driving part 5 rotates the folding members in a pair (first folding member 11 and second folding member 12) and the pivot shaft 13 together in response to the displacement of the pivot shaft 13 by the first driving part 5.

In this case, the displacement of the pivot shaft 13 and the rotations of the folding members in a pair (first folding member 11 and second folding member 12) are linked by the first driving part 5, thereby allowing integration into a single driving source.

Preferably, at the facing position at which the folding surface 10 faces the pad surface 4S, the tip 11T (12T) of the folding surface 10 away from the pivot shaft 13 protrudes further toward the pad surface 4S than the base 11B (12B) of the folding surface 10 close to the pivot shaft 13.

In this case, while the workpiece is pressed against the pad surface by the tip 11T, the base 11B loosely contacts the workpiece in the vicinity of its folding line to curve the workpiece into a shape like a hairpin in the vicinity of the folding line. As a result, the occurrence of creases in the thick workpiece is reduced.

The workpiece may be folded into three.

For example, the center portion $W_C$ of the workpiece W may be held on the pad 4, the first folding member 11 may contact the first end portion W1 of the workpiece W as viewed in the lengthwise direction $W_L$ thereof, and the second folding member 12 may contact the second end portion W2 of the workpiece W as viewed in the lengthwise direction $W_L$. Namely, the first end portion W1 of the workpiece W may be folded by the first folding member 11 and the second end portion W2 of the workpiece W may be folded by the second folding member 12.

Preferably, each of the folding units U further includes the retaining mechanism 2 provided between the first folding member 11 arranged adjacent to the first end portion W1 and the second folding member 12 arranged adjacent to the second end portion W2, the retaining mechanism 2 used for defining a folding line of the workpiece W by facing or contacting an exposed surface $W_S$ of the center portion $W_C$ of the workpiece W.

In this case, the occurrence of fluctuation in the position of the folding line of the workpiece is reduced not only by holding the workpiece on the pad surface but also by the retaining mechanism 2 facing or contacting the exposed surface $W_S$ of the workpiece.

In a preferred folding method, the pressing step and the first folding step are performed by performing the bending step continuously while the folding surface 10 of the first folding member 11 is in surface contact with the first end portion W1 of the workpiece W.

The surface contact of the first folding member 11 with the first end portion W1 facilitates retention of the deformed shape of the workpiece and prevents the workpiece being bent or after being folded from unintentionally restoring its original shape.

More preferably, each of the steps is performed while the center portion $W_C$ of the workpiece W is sucked on the pad surface 4S, the first end portion W1 of the workpiece W is in a non-sucked state of not being sucked on the folding surface 10 of the first folding member 11, and the second end portion W2 of the workpiece W is in a non-sucked state of not being sucked on the folding surface 10 of the second folding member 12 for folding the second end portion W2 of the workpiece W.

In this case, while the center portion of the workpiece is sucked on the pad surface, workpiece is not sucked by the first folding member 11 and the second folding member 12. Thus, even if the workpiece is a thick item, the workpiece is bent loosely into a shape like a hairpin along the folding surface 10 to reduce the occurrence of creases in the workpiece.

The present folding method may further include a second folding step of causing the second folding member 12 to fold the second end portion W2 of the workpiece W so as to stack the second end portion W2 over the folded first end portion W1. Specifically, after the first end portion W1 is folded by the first folding member 11, the second end portion W2 may be folded by the second folding member 12 so as to be stacked over the folded first end portion W1.

Any feature illustrated and/or depicted in conjunction with one of the aforementioned technical ideas or embodiments may be used in the same or similar form in one or more of other technical ideas or other embodiments, and/or may be used in combination with, or in place of, any feature of the other technical ideas or embodiments.

While the preferred embodiments have been described above by referring to the drawings, a person skilled in the art will easily think of various changes and modifications within an obvious range by considering the present description.

For example, the number of the folding units may be two or more.

Thus, such changes and modifications are interpreted as those within a range of the present invention defined from the scope of the claims.

INDUSTRIAL APPLICABILITY

The present invention is applicable to a folding device and a folding method for items such as wearing items that may be napkins and incontinence pads, absorbent items for animals, etc.

REFERENCE SIGNS LIST

10: Folding surface 11B, 12B: Base 11T, 12T: Tip
11, 12: (first, second) Folding member 13: Pivot shaft
2: Retaining mechanism 20: Retaining part 21, 22: (first, second) Retaining plate
2E: End portion
23: Pivot frame 24: Long hole 25: Bolt
F: Front side B: Back side
3: Drum 31: Axis
4: Pad 4S: Pad surface 4H: Suction hole
5: First driving part 6: Second driving part
81, 82: First, second transport device 83: Affixing device
D1: Diameter direction D11: Outer side of diameter direction D2: Width direction
R: Circumferential direction (rotation direction) T: Tape
U: Folding unit
W: Workpiece W1, W2: (first, second) End portion Wb: Folding line $W_C$: Center portion $W_L$: Lengthwise direction $W_S$: Exposed surface

The invention claimed is:

1. A folding device comprising a plurality of folding units arranged in a circumferential direction of a drum that rotates about an axis, each of the folding units including:
a pad for holding a center portion of a workpiece on a pad surface;
a retaining mechanism configured to hold the center portion of the workpiece onto the pad;
a first folding member for folding a first part of the workpiece over the center portion, wherein the first holding member is located on a first side of the pad and has a folding surface;
a first pivot point having a pivot shaft located on the first side of the pad and arranged parallel to the pad surface, wherein:
the first folding member is rotatably coupled to the first pivot point, such that the first folding member is configured to rotate about the first pivot point and exert a force onto the first part of the workpiece with the folding surface of the first folding member to fold the first part over the center portion; and
during the rotation of the first folding member about the first pivot point, the pivot shaft of the first pivot point moves in a direction perpendicular to the pad surface, wherein the first pivot point moves beyond a plane of the pad surface, allowing the folding surface of the first folding member to exert the force onto the first part of the workpiece during the folding of the first part over the center portion;
a second folding member for folding a second part of the workpiece different from the first part over the center portion, wherein the second folding member is located on a second side of the pad opposite the first side of the pad and has a folding surface; and
a second pivot point having a pivot shaft located on the second side of the pad and arranged parallel to the pad surface, wherein:
the second folding member is rotatably coupled to the second pivot point, such that the second folding member is configured to rotate about the second pivot point and exert a force onto the second part of the workpiece with the folding surface of the second folding member to fold the second part over the center portion; and
during the rotation of the second folding member about the second pivot point, the pivot shaft of the second pivot point moves in a direction perpendicular to the pad surface, wherein the second pivot point moves beyond the plane of the pad surface, allowing the folding surface of the second folding member to exert the force onto the second part of the workpiece during the folding of the second part over the center portion.

2. The folding device accoring to claim 1, wherein the folding device is configured to rotate the first folding member and the second folding member until the folding surface reaches the facing position at which the folding surface faces the pad surface after moving the pivot shaft to be positioned on an outer side of the diameter direction outside more than the pad surface.

3. The folding device according to claim 2, wherein the folding device is configured in such a manner that, at the facing position at which the folding surfaces faces the pad surface, a tip of the folding surface away from the pivot shaft protrudes further toward the pad surface than a base of the folding surface close to the pivot shaft.

4. The folding device according to claim 3, wherein the folding device is configured in such a manner that a center portion of the workpiece is held on the pad, the first folding member contacts a first end portion of the workpiece as viewed in a lengthwise direction of the workpiece, and the second folding member contacts a second end portion of the workpiece as viewed in the lengthwise direction.

5. The folding device according to claim 2, wherein the folding device is configured in such a manner that a center portion of the workpiece is held on the pad, the first folding member contacts a first end portion of the workpiece as viewed in a lengthwise direction of the workpiece, and the second folding member contacts a second end portion of the workpiece as viewed in the lengthwise direction.

6. The folding device according to claim 1, wherein the folding device is configured in such a manner that a center portion of the workpiece is held on the pad, the first folding member contacts a first end portin of the workpiece as viewed in a lengthwise direction of the workpiece, and the second folding member contacts a second end portion of the workpiece as viewed in the lengthwise direction.

7. The folding device according to claim 6, wherein the retaining mechanism is provided between the first folding member and the second folding member and the retaining mechanism is used for defining a folding line of the workpiece by facing or contacting an exposed surface of the center portion of the workpiece.

8. The folding device according to claim 1, wherein the folding device is configured in such a manner that, at the facing position at which the folding surface faces the pad surface, a tip of the folding surface away from the pivot shaft protrudes further toward the pad surface than a base of the folding surface close to the pivot shaft.

9. The folding device according to claim 8, wherein the folding device is configured in such a manner that a center portion of the workpiece is held on the pad, the first folding member contacts a first end portion of the workpiece as viewed in a lengthwise direction of the workpiece, and the second folding member contacts a second end portion of the workpiece as viewed in the lengthwise direction.

10. The folding device according to claim 1, wherein the folding device is configured in such a manner that a center portion of the workpiece is held on the pad, the first folding member contacts a first end portion of the workpiece as viewed in a lengthwise direction of the workpiece, and the second folding member contacts a second end portion of the workpiece as viewed in the lengthwise direction.

* * * * *